(12) United States Patent
Huang et al.

(10) Patent No.: US 12,343,404 B2
(45) Date of Patent: Jul. 1, 2025

(54) LIGAND-TARGETED CELL CONJUGATE (LTCC)-BASED ANTI-TUMOR IMMUNE CELL

(71) Applicants: AFFILIATED HOSPITAL OF JIANGNAN UNIVERSITY, Jiangsu (CN); JIANGNAN UNIVERSITY, Jiangsu (CN)

(72) Inventors: Zhaohui Huang, Jiangsu (CN); Zhimeng Wu, Jiangsu (CN); Liang Gong, Jiangsu (CN); Yanchun Li, Jiangsu (CN)

(73) Assignee: AFFILIATED HOSPITAL OF JIANGNAN UNIVERSITY, Jiangsu (CN)

( * ) Notice: Subject to any disclaimer, the term of this patent is extended or adjusted under 35 U.S.C. 154(b) by 766 days.

(21) Appl. No.: 17/551,412

(22) Filed: Dec. 15, 2021

(65) Prior Publication Data
US 2022/0202949 A1  Jun. 30, 2022

(30) Foreign Application Priority Data
Dec. 28, 2020  (CN) .......................... 202011578778.2

(51) Int. Cl.
| | | |
|---|---|---|
| *A61K 47/69* | (2017.01) | |
| *A61K 40/15* | (2025.01) | |
| *A61K 40/42* | (2025.01) | |
| *A61K 47/68* | (2017.01) | |
| *A61P 35/00* | (2006.01) | |
| *C12N 5/0783* | (2010.01) | |

(52) U.S. Cl.
CPC .......... *A61K 47/6901* (2017.08); *A61K 40/15* (2025.01); *A61K 40/4204* (2025.01); *A61K 47/6851* (2017.08); *A61P 35/00* (2018.01); *C12N 5/0646* (2013.01); *A61K 2239/31* (2023.05); *A61K 2239/38* (2023.05)

(58) Field of Classification Search
CPC ........ A61K 47/6901; A61K 39/464404; A61K 47/6851; A61P 35/00; C12N 5/0646
See application file for complete search history.

(56) References Cited

FOREIGN PATENT DOCUMENTS

| CN | 108265027 A | * | 7/2018 | ............. A61K 35/17 |
|---|---|---|---|---|
| CN | 110420334 A | * | 11/2019 | ............. A61K 38/07 |
| CN | 111235106 A | | 6/2020 | |
| CN | 111534475 A | * | 8/2020 | ......... A61K 2239/31 |
| CN | 111718904 A | | 9/2020 | |

OTHER PUBLICATIONS

Li et al. CN111534475A. Machine translation.2020. (Year: 2020).*
Zhou et al. CN108265027A. Machine translation.2018. (Year: 2018).*
Wu et al. CN111534475A. Machine translation.2019. (Year: 2019).*

* cited by examiner

*Primary Examiner* — Elly-Gerald Stoica
(74) *Attorney, Agent, or Firm* — HAUPTMAN HAM, LLP

(57) ABSTRACT

Non-natural sugars modified with a bioorthogonal reactive group are added into a culture medium of immune cells such as NK cells to obtain immune cells modified with the bioorthogonal reactive group; and then, under a physiological condition, a targeting ligand, for example, a nanobody, is modified to a surface of each of the immune cells through a bioorthogonal reaction, wherein the targeting ligand has one terminal with a bioorthogonal reactive pairing group which is capable of being matched and connected with the bioorthogonal reactive group to generate a connecting reaction, connection is implemented by a transpeptidase SrtA-mediated chemoenzymatic method. The targeting ligand highly specifically recognizes and binds to a highly expressed receptor on the surface of tumor cells. The immune cell modified with the targeting ligand can specifically bind in a targeted way to the tumor cells, therefore generating cytokines, killing and damaging tumor cells.

4 Claims, 4 Drawing Sheets

LIGAND-TARGETED CELL CONJUGATE (LTCC)-BASED ANTI-TUMOR IMMUNE CELL

BACKGROUND OF THE INVENTION

1. Technical Field

The invention belongs to the technical field of biomedical engineering, and in particular, relates to a ligand-targeted cell conjugate (LTCC)-based anti-tumor immune cell, as well as a preparation method and use thereof.

2. Description of Related Art

Cancer remains the number one threat to human life and ranks second in the list of causes of human death. The International Agency for Research on Cancer shows 19.30 million new cancer cases and a 10.00 million death toll in the world in 2020, including 4.57 million new cancer cases and a 3.00 million death toll in China, which both take the top position globally.

Cancer immunotherapy is hailed as the third revolution of cancer treatment and is currently the most popular treatment method under study. Adoptive cellular therapy is a frequently used immunotherapy, which is mostly represented by modification of immune cells in vitro and then delivery of the immune cells back into a patient's body for treatment. The delivery involves autologous cells and xenogenous cells. Immune cells include natural killer cells (NK cells), T cells, macrophages, etc. In particular, NK cells, as the most important cells in the innate immune system, do not rely on a specific antigenic stimulus, but have natural anti-tumor and anti-infectious abilities. With a relatively short life span in cycles, NK cells do not cause a dangerous cytokine storm which is usually seen in the immunotherapy based on T cells. However, to perform functions thereof, NK cells are required to keep close contact with tumor cells. After binding to targeted cells, NK cells secrete and release cytotoxic granules such as perforin and granzyme, and without restrictions by the major histocompatibility complex, express a tumor necrosis factor-related apoptosis-inducing ligand, thereby inducing pore formation on the surfaces of tumor cells to result in lysis and death of cells.

Immune cells such as NK cells and T cells have a good tumor-killing activity, but lack the ability of binding in a targeted way to the tumor cells. In addition, particularly, some tumor cells have developed an immune escape mechanism which causes a great trouble to tumor treatment.

To solve this problem, a chimeric antigen receptor (CAR) technology which is used to modify the immune cells for tumor treatment has drawn attention from many researchers, and two most representative CAR-T cells, namely Kymriah and Yescarta, have been approved by American FDA for clinical use in 2017. In view of this, many researchers consider use of the CAR technology for engineering of NK cells. No CAR-NK cell product is currently available on the market, yet at least 19 articles regarding CAR-NK related clinical study have been found in the website clinicaltrials.gov. These articles all disclose the clinical study at the first/second stage, and target at cancers including solid tumors, hematological malignancies and lymphomas. Recently, reports on CAR-modified macrophages (CAR-M) have also been seen. The targeting ligand modified with the CAR technology is generally a single-chain variable Fragment (scFv), but such antibody fragment has a low affinity and poor stability, so that the application of scFv-CAR-NK cells faces some limitations. In addition, modification of the immune cells using aptamers and target peptides is also found in early reports. However, the aptamer as a single stranded oligonucleotide is easily attacked in vivo by a nuclease to degrade and get inactive; while the target peptide as a polypeptide with only dozens of amino-acid residues has a simple structure and has a limited ability of recognizing and binding to receptors on the tumor cells in the in-vivo multi-cell environment.

Targeting ligands are biomacromolecules, including nanobodies (Nbs), aptamers, scFv, glycoside ligands, target peptides, etc., which can specifically recognize and bind to the highly expressed receptors on surfaces of the tumor cells.Nbs The Nb is an antibody naturally existing in camelidae and shark serums. With a molecular weight of approximately 15 kDa (half of the molecular weight of the scFv), the Nb is the smallest antibody known currently, and genes thereof evolve from the type-III sub-family of human VH genes. The genes of the Nb and the type-III sub-family of human VH genes are highly homological. However, the Nb has 4 to 9 more amino-acid residues in a CDR3 zone than the human antibody does, so that the Nb can form a special convex ring structure which can recognize more larvaceous antigenic determinants. In addition, four hydrophobic amino acids in an FR2 zone of the Nb mutate into hydrophilic amino acids, greatly increasing the water-solubility of the Nb; and at the same time, a disulfide bond in the Nb greatly enhances the resistance of the Nb to heat, acids and alkali. Modification of NK cells and even other immune cells using the targeting ligands such as the Nb can obviously improve the targeting ability of the immune cells and further achieve a good tumor treatment effect.

The first article (doi:10.3390/cells9020321) which discuses modification of NK cells with the Nb has been seen in early 2020. The author disclosed that modification of the primary NK cells (separated from human peripheral blood) with the Nb by means of the CAR technology contributed to Nb-CAR-NK cells with good anti-tumor activities. However, the implementation of the CAR technology requires mediation by retroviruses such as slow viruses to incorporate foreign plasmids into NK cells. Such genetic manipulation generates a risk of inserting virogenes into normal cell genomes, and therefore has certain potential safety hazards. Moreover, separation and augmentation of the primary NK cells consumes much time and labor. Therefore, it is greatly significant to develop a convenient, safe and effective anti-tumor NK cell.

A new biochemical technology which combines glucose metabolic engineering and click chemistry has been developed in recent years. Such technology can be used to specifically modify many cells. According to a large number of literatures, the general process of such technology is as follows: first, azido sugars are absorbed through cells, such that the cells carry the azide groups; and then, the aptamers, chemical drugs or fluorescent groups which are conjugated with the alkynyl (for example the DBCO or terminated alkynyl) are catalyzed with or without copper to enable the cells to connect with specific genes. In the above-mentioned alkynyl modification process, pure chemical synthesis is implemented. However, since a great amount of organic reagents are used as solvents during the pure chemical syntheses, the above-mentioned method is not applicable when the alkynyl is used to modify proteins such as the Nbs, the scFv and conventional antibodies. Therefore, a more efficient and moderate enzymatic method is required to perform connection.

SUMMARY OF THE INVENTION

Objectives of the invention: to overcome defects in prior art, the invention provides a preparation method and use of an LTCC-based anti-tumor immune cell, in particular a preparation method and use of a Nb-cell conjugate (NBCC)-based anti-tumor immune cell. On the premise of no genetic manipulation, a technology which is used to covalently load targeting ligands including Nbs to cell surfaces through metabolic pathways of cells and by a series of chemoenzymatic methods is called LTCC, and when Nbs are used as targeting ligands, such technology can be called NbNBCC.

To achieve the above objective, a technical solution adopted by the invention is as follows.

An LTCC-based anti-tumor immune cell is provided, wherein a targeting ligand and an immune cell which are respectively modified with a bioorthogonal reactive pairing group and a bioorthogonal reactive group on the surface are connected through a bioorthogonal reaction to form a targeting immune cell which is conjugated with the targeting ligand on the surface, and the targeting ligand performs specific recognition and is connected with a highly expressed receptor on the surface of the tumor cell.

Further, targeting ligands are biomacromolecules, including but not limited to, Nbs, aptamers, single-chain variable Fragments (scFv), glycoside ligands, target peptides, etc.

Further, immune cells include NK cells, T cells and macrophages, and NK cells include but are not limited to, an NK92-MI cell line, an NK 92 cell line and primary NK cells isolated from human bodies.

Further, the bioorthogonal reactive pairing group and the bioorthogonal reactive group on the non-natural sugars are used in pair; bioorthogonal reactive groups include but are not limited to an azide group, a ketone/aldehyde group, an alkylene, and a cycloalkyne, and the corresponding bioorthogonal reactive pairing group is an alkynyl compound, a hydroxylamine, a tetrazolium compound or a tetrazine compound, wherein alkynyl compounds include but are not limited to dibenzocyclooctyne (DBCO) for a copper-free catalysis, difluorinated cyclooctyne (DIFO), biarylazacyclooctynones (BERAC) and compounds with a terminated alkynyl for copper catalysis. The structural component of the functionalized Nb in the invention is: Nb-PEGn-bioorthogonal reactive pairing group, wherein the bioorthogonal reactive pairing group is a functional group which can perform the bioorthogonal reaction (also called chemical modification of live cells) together with the bioorthogonal reactive group which modifies the non-natural sugars; when the bioorthogonal reactive group is the azide group, the corresponding bioorthogonal reactive pairing group is the terminated alkynyl compound including but not limited to dibenzocyclooctyne (DBCO), difluorinated cyclooctyne (DIFO), biarylazacyclooctynones (BERAC) and so on; when a marked group is the ketone/aldehyde group, the corresponding bioorthogonal reactive pairing group is a hydrazine or hydroxylamine; and when the bioorthogonal reactive group is the alkylene, the corresponding bioorthogonal reactive pairing group is a tetrazolium group; and when the bioorthogonal reactive group is the cycloalkyne, the corresponding bioorthogonal reactive pairing group is a tetrazine group, and so on.

Further, non-natural sugars are monosaccharoses modified with the bioorthogonal reactive group, including but not limited to N-azidoacetylmannosamine-tetraacylated (Ac$_4$ManNAz), N-azidoacetylgalactosamine-tetraacylated (Ac$_4$GalNAz), N-azidoacetylglucosamine-tetraacylated (Ac$_4$GlcNAz), N-azidoacetylmannosamine-acetylated (ManNAz), N-azidoacetylneuraminic acid (SiaNAz), N-levulinoylmannosamine (ManLev), and N-propionylmannosamine-acetylated (Ac$_4$ManLev).

A second objective of the invention is to provide a preparation method of the LTCC-based anti-tumor immune cell. The preparation method includes: adding non-natural sugars modified with a bioorthogonal reactive group into a culture medium of immune cells, culturing to obtain immune cells modified with the bioorthogonal reactive group; modifying a surface of each of immune cells using a functionalized targeting ligand, which is synthesized by a chemoenzymatic method, through a bioorthogonal reaction under a biological condition to form a targeting immune cell, wherein the functionalized targeting ligand has one terminal carrying a bioorthogonal reactive pairing group.

Further, the synthesis method of the functionalized targeting ligand is as follows: one terminal of the bioorthogonal reactive pairing group is connected with a polyethylene glycol (PEG) linker and a triglycine peptide with a free amino group through chemical synthesis, such that the bioorthogonal reactive pairing group meets the condition of connection with a transpeptidase Sortase A, wherein PEG includes but is not limited to PEG4 with four degrees of polymerization; biological expression or chemical synthesis is implemented to enable a primordial targeting ligand to have one terminal containing a site capable of being recognized by LPXTG transpeptidase Sortase A, wherein X represents any amino acid apart from cysteine; by the effect of the transpeptidase Sortase A, the bioorthogonal reactive pairing group, which is connected with the triglycine peptide with a free amino group and the PEG4, is connected with the primordial targeting ligand which has one terminal carrying amino acid sequence of LPXTG; a reaction proceeds at 16° C. for 5-9 hours, and purification is executed with nickel-ion magnetic beads to synthesize the functionalized targeting ligand.

Further, the bioorthogonal reactive pairing group has one terminal connected with the PEG linker and the triglycine peptide with the free amino group through an amide condensation reaction.

Further, the bioorthogonal reaction condition is that the immune cell modified with the bioorthogonal reactive group is mixed with the functionalized targeting ligand, and the bioorthogonal reaction proceeds in systems including but not limited to phosphate buffer saline (PBS) or normal saline.

A third objective of the invention is to provide use of the LTCC-based anti-tumor immune cell in preparation of cancer drugs, wherein cancers treated using the cancer drugs contain target points capable of being specifically recognized by the targeting ligand, including solid tumors, blood tumors and lymphomas.

Beneficial effects: Compared with prior art, the invention has the following beneficial effects:

1. The LTCC, in particular the NBCC, provided by the invention is a new technology based on technologies such as fermentation engineering, glucose metabolic engineering, the chemoenzymatic method, etc. This technology does not involve use of any genetic manipulation means and virus infection technologies, and is very safe. Meanwhile, this technology can allow protein type biological active molecules such as the Nb which can be used as the targeting ligand to be quickly and conveniently connected with the immune cells, and integrate the respective advantages of the targeting ligand and the immune cell to achieve a "1+1>2" effect, and greatly increases the targeted-connection and tumor-killing abilities of the immune cells.

2. The LTCC, in particular the NBCC, provided by the invention is quite universal, and can enable the immune cells to kill and damage all tumor cells simply by changing the category of the targeting ligand, for example change into the Nb. In addition, since pathways of glucose metabolism of all cells are highly conservative, so this technology can be applied to modification of the targeting ligands of all cells, such as the Nb.

3. Immune cells used according to the invention include various NK cells, T cells, macrophages, etc., wherein NK cells are usually cell lines such as NK92-MI which are easily cultured. Compared with the majority of NK cells for study which are separated from human peripheral blood, the NK92-MI cell line is easily cultured by a large number and industrialized, and has a good prospect of application.

DETAILED DESCRIPTION OF PREFERRED EMBODIMENTS OF THE INVENTION

Figure 1:
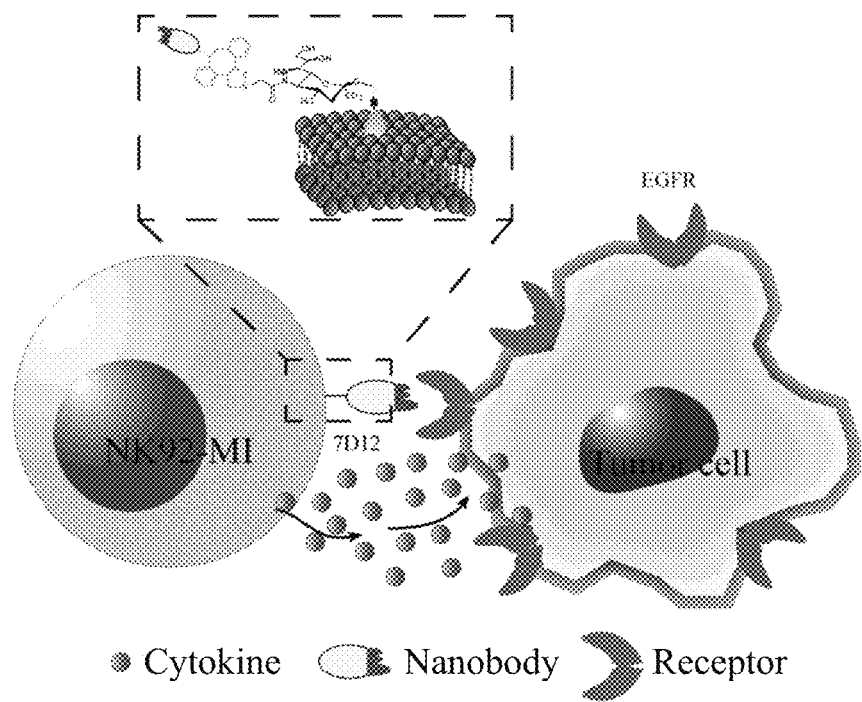
FIG. 1 is a schematic diagram of the principle process according to the invention.

To facilitate understanding of the technical means, objectives and effects of the invention, the invention is further described with reference to, but not limited by, the following embodiments.

Embodiment

The invention can be better understood according to the following embodiments. However, it is understandable for a skilled in the art that, the specific material proportions, technological conditions and results described in the embodiments apply to the invention only, and should not be construed as limiting the protective scope of the invention.

An objective of the invention is to disclose a preparation method and use of an LTCC-based anti-tumor immune cell. In the embodiments, a Nb 7D12, as a targeting ligand, and NK cells, as examples of immune cells, are used to fully interpret and describe preparation and application of the anti-tumor NK cells using NBCC. NK cells used belong to an NK92-MI or NK92 cell line which is generally called "off-the-shelf reagent". Such approach facilitates cell acquisition, cultivation and augmentation in a large scale, and subsequent conversion into production. The following embodiments are not limited to the two types of NK cells, and immune cells including other NK cells, T cells and macrophages can also be used; similarly, the targeting ligand is also not limited to the Nb 7D12, and can be other Nbs or macromolecules with targeting and specific recognition functions, for example, aptamers, scFv, glycoside ligands, target peptides, etc.

Embodiment 1: Preparation of a Functionalized Nb

Preparation of a functionalized Nb includes three procedures, namely fermentation and purification of a Nb, chemical synthesis of a bioorthogonal reactive group which carries a triglycine peptide, and Sortase A enzyme-mediated connection.

Fermentation and Purification of the Nb:

100 μL of previously prepared glycerol frozen bacteria of engineered *Escherichia coli* which were able to produce a Nb 7D12 (targeting at EGFR) was inoculated in 25 mL of an LB culture medium which contained 100 μg/mL kanamycin, and the bacteria in the LB culture medium were cultured and activated at 37° C. and at 200 rpm overnight. On the second day, 2% of the bacteria were transferred into a TB culture medium which contained 100 μg/mL kanamycin and cultured at 37° C. and at 200 rpm, wherein the formula of the TB culture medium included 12 g/L peptone, 24 g/L yeast powder, 5 g/L glycerol, 16.4 g/L $K_2HPO_4·3H_2O$ and 2.31 g/L $KH_2PO_4$. After $OD_{600}$ reached 0.6 to 0.8, IPTG with a final concentration of 0.2 mM was added to induce expression at 16° C. for 24 hours. After fermentation was ended, the bacteria were collected through centrifugation at 8000 rpm. An ultrasonication lysis buffer was added for ultrasonication (the buffer was prepared according to the description of a nickel column required subsequently); then centrifugation was carried out at 12000 rpm and 4° C. for 15 min; and supernatant was collected and repeatedly centrifuged for 3 times. Subsequently, the nickel column was placed in the supernatant to purify the Nb 7D12, and finally, a gel column G25 for desalination was used to remove imidazolium salt.

Chemical Synthesis:

1) Synthesis of azido sugars: 1.22 g of mannosamine hydrochloride was dissolved in 50 mL of MeOH; then, 1.06 mL of 30% NaOMe/MeOH solution was added; next, the mixed materials were stirred for 1 hour at room temperature; later, 0.815 mL of TEA and 2.9 g of chloroacetic anhydride were added; next, the mixed substance was stirred and reacted at room temperature for 6 hours; the obtained solution was eluted by gradient using $CH_2Cl_2$ and MeOH at a ratio from 6:1 to 5:1 through the gel column to obtain N-chloracetyl mannosamine; after a solvent volatilized, 16 mL of DMF and 3.68 g of $NaN_3$ were added; the solution reacted at 80° C. for 4 hours; after the solvent volatilized as the solution cooled to room temperature, 30 mL of pyridine and 15 mL of acetic anhydride were added; the solution was stirred at room temperature and was kept overnight for reaction; then, 200 mL of ethyl acetate was added into the reacting solution; the mixed solution was mixed well; 100 mL of 1M hydrochloric solution was added into an organic layer for washing; the solution was separated after three times of washing; next, 100 mL of saturated $NaHCO_3$ was added to wash the solution for three times, then the solution was separated again; 100 mL of saturated NaCl was added to wash the solution twice, and then the solution was separated one more time; next, anhydrous $Na_2SO_4$ was added to dry the substance, and the dried substance was eluted by gradient using n-hexane and ethyl acetate at a ratio from 1:1 to 1:2 through the gel column to obtain the product $Ac_4ManNAz$.

In addition to the previously prepared N-azidoacetylmannosamine-tetraacylated ($Ac_4ManNAz$), non-natural sugars applicable to the invention further include: N-azidoacetylgalactosamine-tetraacylated ($Ac_4GalNAz$), N-azidoacetylglucosamine-tetraacylated ($Ac_4GlcNAz$), N-azidoacetyl-mannosamine-acetylated (ManNAz), N-azidoacetylneuraminic acid (SiaNAz), N-levulinoylmannosamine (ManLev), and N-propionylmannosamine-acetylated ($Ac_4ManLev$), etc., wherein parent materials of corresponding sugars are respectively used as raw materials. Similarly, those sugars can also be prepared through above-mentioned chemical synthesis.

Figure 2:
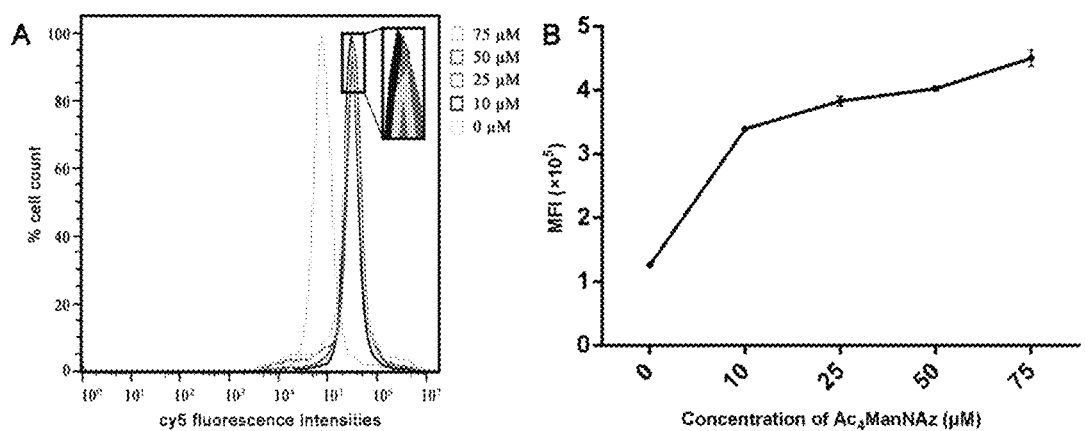
FIG. 2 is a schematic diagram of screening of an optimal $Ac_4ManNAz$ concentration; A is a displacement diagram of flow cytometry, and B is a fluorescence quantitative analysis diagram.

According to the embodiments of the invention, as shown in FIG. 2, it can be seen that the optimal concentration of the added non-natural sugars is 50 to 100 μM with reference to the displacement effect of the flow cytometry and results of the quantitative fluorescence analysis.

Figure 4:
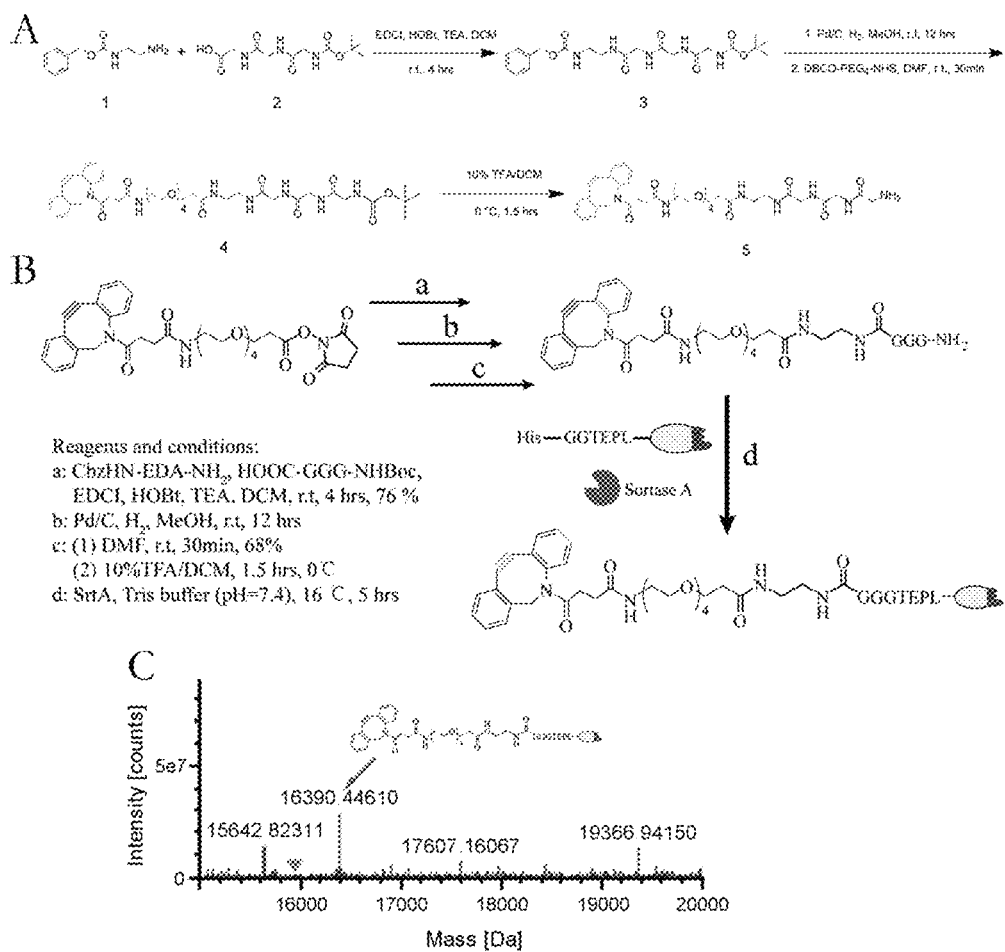
FIG. 4 is schematic diagram of a functionalized targeting ligand with a Nb synthesized by a chemoenzymatic method; A is a full flowchart of chemical synthesis of DBCO-PEG4-GGG, B is a flowchart of synthesis of DBCO-PEG4-7D12 by connection of the DBCO-PEG4-GGG and a Nb 7D12 using sortaseA, C is a schematic diagram of mass spectrum identification of a connected product DBCO-PEG4-7D12 (theoretical molecular weight is 16391.5; and an observed value of mass spectrum is 16390.4).

2) Synthesis of DBCO-PEG4-GGG: the entire process can be seen in FIG. 4A. Ethylenediamine with one terminal protected by a Cbz group and triglycine peptide with one terminal protected by a Boc group jointly performed an amide condensation reaction at an equivalent proportion of 4:5 to 4:7; after removal of the Cbz group, the reacting product reacted with DBCO-PEG4-NHS at an equivalent proportion of 2:1 to 1:1; and finally, the product DBCO-$PEG_4$-GGG was obtained after removal of the Boc group.

The specific method is as follows:

310 mg of Cbz-EDA-$NH_2$, 578 mg of Boc-GGG-COOH (Boc: t-Butyloxy carbonyl), 411 mg of HOBt, 0.6 mL of TEA, and 573 mg of EDC.HCl were mixed well in 10 mL of DMF at 0° C.; the mixed materials were stirred at room temperature for 4 hours; then, DCM and saturated NaCl were used for extraction and liquid separation; then, anhydrous $Na_2SO_4$ was added for drying; next, the dried substance was purified through silica column chromatography using a chromatographic liquid which was composed of DCM and MeOH at a ratio of 50:1; then, 20 mL of MeOH and 120 mg of Pd/C were added; the mixed substance was stirred with the existence of hydrogen gas at room temperature for 12 hours for removal of the Cbz group; and Boc-GGG-EDA-$NH_2$ was obtained after purification and spin drying. 70 mg of Boc-GGG-EDA-$NH_2$ was dissolved in 10 mL of DMF; then, 140 mg of DBCO-$PEG_4$-NHS was added; the mixed material was stirred for reaction for 30 min at room temperature; after the reaction ended, the reacting product was purified through silica column chromatography using a chromatographic liquid which was composed of DCM and MeOH at a ratio of 10:1. Then, 20% TFA/DCM was added, and the Boc group was removed by stirring stirred for 1.5 hours at room temperature; finally, a proper amount of toluene was added, and reduced pressure distillation was carried out to obtain DBCO-$PEG_4$-GGG-$NH_2$.

Sortase A enzyme-mediated conjugation: the entire process can be seen in FIG. 4B. The Nb was expressed by *Escherichia coli*, and a carboxyl terminal carried a site capable of being recognized by LPXTG (X was any amino acid, for example E/A/V, etc.) transpeptidase Sortase A, and a histidine tag (His tag). During Sortase A enzyme-mediated connection, 20-25 μM of the targeting ligand, i.e. the Nb, 250-500 μM of micromolecular substrate containing a bioorthogonal reactive group, and 3-5 μM of transpeptidase Sortase A were mixed and reacted at 16° C. for 5-9 hours in a Tris-HCl/NaCl buffer which had a pH value of 7.4-7.5 and contained $CaCl_2$). Then, the reaction product was purified using magnetic beads coated with nickel-ion or agarose column bearing nickel-ion; and finally, the gel column G25 was used to remove micromolecules such as the bioorthogonal reactive group by steps of dechlorination.

The reaction system included: 20 μM of 7D12, 500 μM of DBCO-$PEG_4$-GGG-$NH_2$, 5 μM of enzyme Srt A, and 1×Srt A reaction buffer solution (formula: 50 mM Tris, 150 mM NaCl, and 5 mM $CaCl_2$), pH in the range of 7.4-7.5). Materials were added according to the above system. After being mixed well, the materials reacted at 16° C. for 5 hours; then, 7D12, Srt A and cut His tag, which did not react, were extracted using magnetic beads coated with nickel-ion; the supernatant was collected and eluted with the gel column G25 to remove excessive DBCO-$PEG_4$-GGG-$NH_2$, and then DBCO-$PEG_4$-7D12 was obtained.

Embodiment 2: Influences of Azido Sugars on Activities of NK Cells

This embodiment describes validation of influences of the added non-natural sugars on cell activities. The specific method is as follows: non-natural sugars were absorbed by cells; the cells were cultured for a period of time; then, $OD_{450}$ was determined using a cell counting kit 8 (CCK8) (Beyotime), and a difference in cell activities of a group added with sugars and a group without sugars was analyzed.

Figure 3:
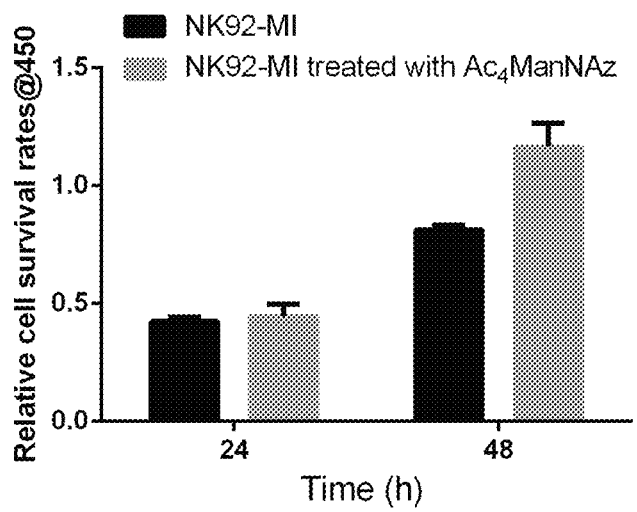
FIG. 3 is a schematic diagram of influences of $Ac_4ManNAz$ on activities of NK92-MI cells.

The specific process is as follows: $1\times10^5$ pieces of NK cells were laid in a 96-pore plates; 0.1% DMSO was added into a control group, while $Ac_4ManNAz$ with a final concentration of 50 μM (the mount of the DMSO was equivalent to 0.1%) was added into an experimental group; then, the cells were cultured in an incubator at 37° C., and subsequently added with the CCK8 after 24 hours and 48 hours respectively; and after 2-hour incubation, $OD_{450}$ was detected using a microplate reader. The results, as shown in FIG. 3, show that, the added non-sugars were not toxic to cells, but slightly promoted growth.

Embodiment 3: Modification of Immune Cells Such as NK Cells with Nb

This embodiment describes acquisition of NK cells with an azide tag and modification with 7D12. The principle process is as shown in FIG. 1. Non-natural sugars were absorbed; a bioorthogonal reactive group which modified the sugars were loaded to cell surfaces through glucose metabolism engineering processes including glucolysis and sialic acid metabolism; then cells were collected, and under a condition similar to the physiological condition, added with the functionalized Nb ($1\times10^4$ pieces of NK cells treated using 8-10 μg of functionalized Nb), and the mixture reacted at 37° C. for 1-1.5 hours. Whether the cells were successfully modified with the Nb was validated through immunofluorescence.

The specific method is as follows:

The previously chemically synthesized $Ac_4ManNAz$ was dissolved in DMSO to prepare a 50 mM parent solution; after filtration and sterilization, 1‰ of the mixed solution was added into a special culture medium special for NK cells to enable the culture medium to contain 50 μM non-natural sugars; NK92-MI cells were cultured in the culture medium for 48 hours and then centrifuged at 600 rpm for 5 min; and, the cells were collected and washed with PBS for 3 times to obtain NK cells modified with the bioorthogonal reactive group N3 (N3-NK92MI).

Next, 8.2 μg of $DBCO-PEG_4-7D12$ was added into every 10000 pieces of cells; the mixed substance reacted at 37° C. for 1.5 hours in the PBS system; and finally, the reacting product was washed with the PBS for 3 times to obtain the functionalized NK cells with 7D12 (7D12-NK92MI).

Figure 5:
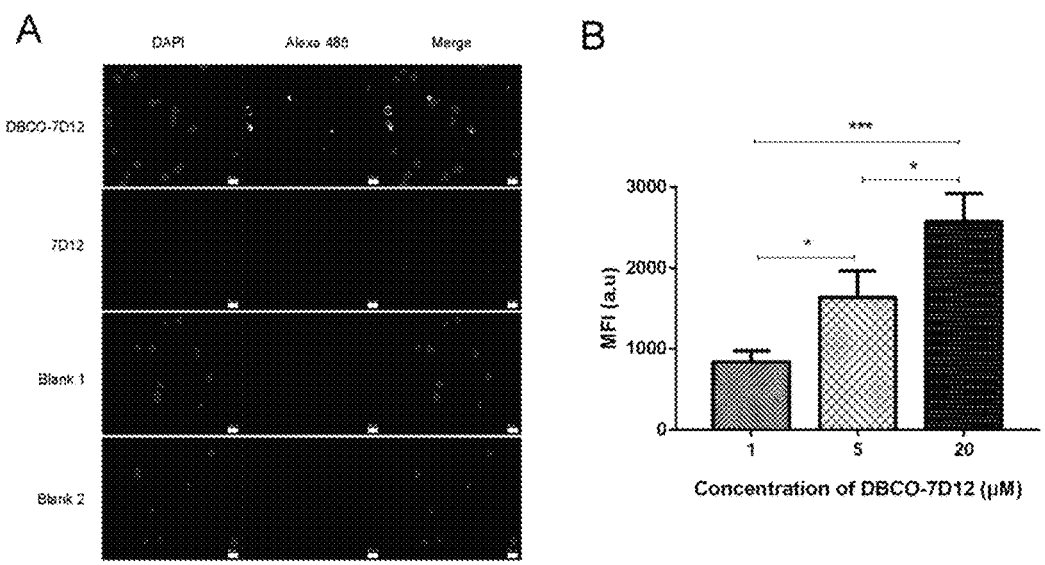
FIG. 5 is schematic diagram of detection after cells are loaded with the Nb 7D12; A is a schematic diagram of observation by laser confocal microscopy, and B is a schematic diagram of screening of the optimal concentration for loading of the DBCO-PEG4-7D12.

The obtained functionalized NK cells (7D12-NK92MI) were displayed through immunofluorescence, as shown in FIG. 5, which represented that modification with 7D12 succeeded.

Embodiment 4: In-Vitro Targeting Detection of the Nb-Functionalized Immune Cells.Nb This embodiment describes analyses of the in-vitro targeting property and anti-tumor activities of the Nb-functionalized immune cells Nb(7D12-NK92MI) obtained in Embodiment 3. The specific method is as follows: NK cells and targeted tumor cells were marked with two colors of fat-soluble dyes respectively; after adherence of the targeted tumor cells, NK cells which were not modified with the Nb and NK cells which were modified with the Nb were respectively cultured together with the targeted tumor cells at an effect-target ratio of 1:1, and the tumor cell adhering ability of the immune cells modified with the Nb was observed through fluorescence imaging.

The following process is as follows:

First, NK92MI/7D12-NK92MI cells were marked with green fluorescent DiO, and high-EGFR-expression LOVO cells which are kept overnight for adherence were marked with red fluorescent DiR; then, NK cells and LOVO cells were mixed at a ratio of 1:1 and cultured for 2 hours; the obtained product was washed with the PBS, fixed, and then re-washed with the PBS, and finally imaged through laser confocal.

Figure 6:
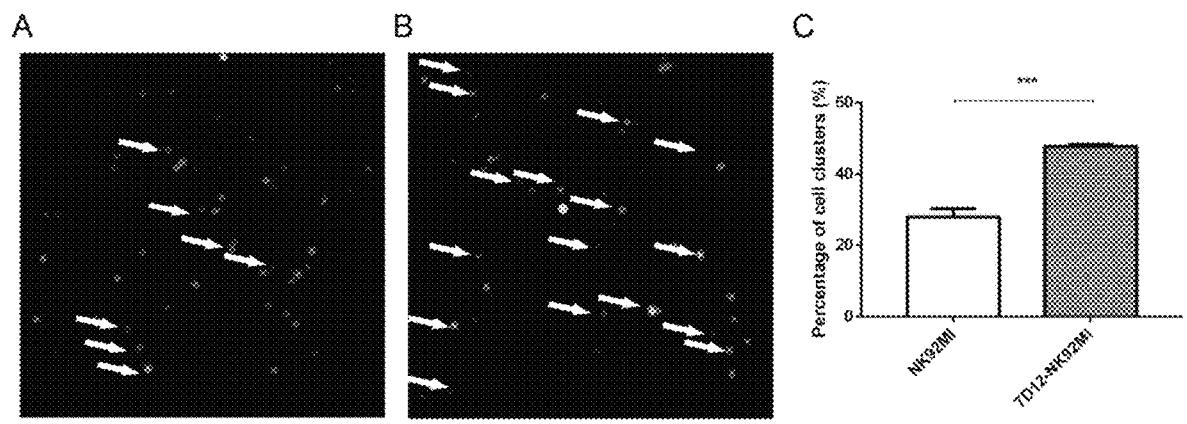
FIG. 6 is a schematic diagram of in-vitro targeting property validation of 7D12-NK92MI cells; A is a schematic diagram of affinity between cancer cells with positive EGFR and NK92-MI cells. B is a schematic diagram of connection between cancer cells with positive EGFR and 7D12-NK92MI cells, and C is a statistical diagram of the connection rate of the above-mentioned groups.

Results show that, the rate of connection between the 7D12-NK92MI cells and the LOVO cells is obviously higher than that between the NK92MI cells and the LOVO cells (FIG. 6), reaching about 48%. The results indicate that, the 7D12 is able to greatly enhance the tumor-binding ability of the NK92MI cells, and the functionalized immune cells modified with the Nb have higher tumor cell adhering ability.

Embodiment 5: In-Vitro Anti-Tumor Activity Detection of the Functionalized Immune Cells with the Nb This embodiment describes analyses of the in-vitro anti-tumor activity detection of the functionalized immune cells (7D12-NK92MI) with the Nb obtained in Embodiment 3. The specific method is as follows: NK cells which were not modified with the Nb and NK cells which were modified with the Nb were respectively cultured together with the targeted tumor cells at different effect-target ratios; the supernatant was collected and cultured; and the tumor cell killing ability of the immune cells was determined through LDH (lactic dehydrogenase).

Figure 7:
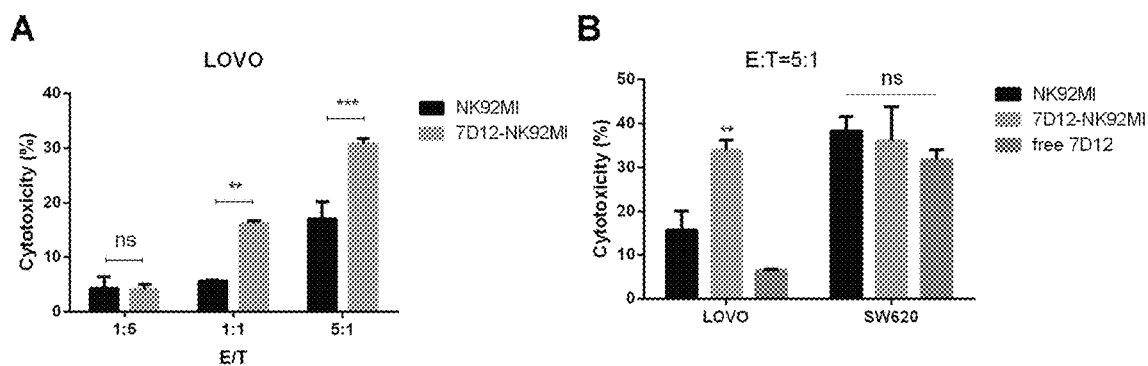
FIG. 7 is a schematic diagram of in-vitro anti-tumor activities of NK92-MI cells modified with the Nb; A is a schematic diagram of comparison of anti-tumor activities at different effect-target ratios, and B is a schematic diagram of essentiality validation of the Nb in cell-killing activities.

The specific process is as follows: NK92MI cells or 7D12-NK92MI cells were cultured together with LOVO cells at the effect-target ratios of 1:5, 1:1 and 5:1 respectively; and then, and the cell-killing ability of NK cells was determined through CytoTox 96 Non-Radioactive Cytotoxicity Assay. As shown in FIG. 7, as the effect-target ratio rises, the tumor-killing ability obviously increases, and the activity of the NK92MI cells modified with the 7D12 is apparently higher than that of the NK92MI cells without the 7D12.

Then, LOVO cells which highly expressed EGFR and SW620 cells which lowly expressed EGFR were used to analyze whether the increase in the tumor-killing ability resulted from the Nb 7D12. As shown in FIG. 7B, NK92MI cells which are modified with the 7D12 and NK92MI which are not modified with the 7D12 are not obviously different in SW620 killing ability, while the LOVO cell-killing activity of the 7D12-NK92MI cells is obviously higher than that of the NK92MI cells.

In addition, through competitive analysis (free 7D12) as shown in FIG. 7B, LOVO cells were treated with free Nb 7D12, and then the treated cells were cultured together with 7D12-NK92MI cells. The result indicates an obvious decline in tumor-killing activity.

Figure 8:
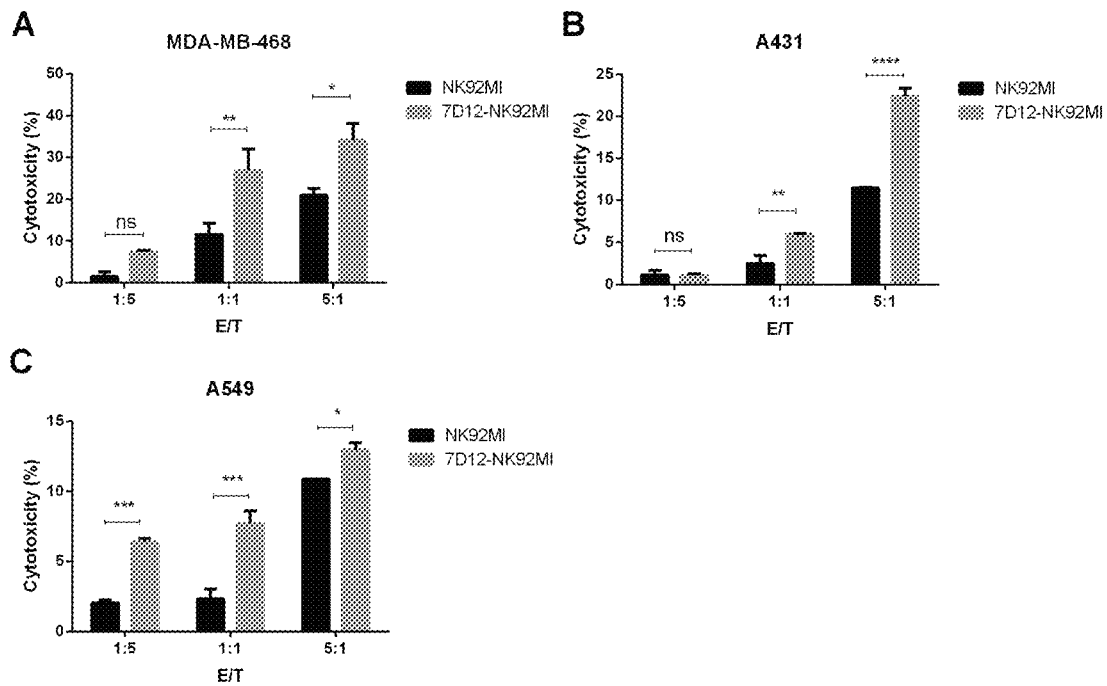
FIG. 8 is a schematic diagram of broad anti-tumor spectrum analysis of NK92-MI cells modified with the Nb.

Several other types of high-EGFR-expression tumor cells, for example, MDA-MB-468 (mammary cancer), A431 (cutaneous squamous carcinoma), A549 (lung cancer) were used to analyze the anti-tumor spectrum of the 7D12-NK92MI cells. The results as shown in FIG. 8 indicate that NK92MI cells engineered with the 7D12 are able to obviously skill the several types of cancer cells.

Results of the embodiment show that, NK cells modified with the Nb are superior to NK cells which are not modified with the Nb in the ability of killing various tumor cells, and have a broad anti-tumor spectrum at the same time.

Embodiment 6: In-Vivo Anti-Tumor Activity of the Functionalized Immune Cells with the Nb In this embodiment describes detection of the in-vivo anti-tumor activity of the functionalized immune cells with the Nb (7D12-NK92MI) obtained in Embodiment 3. The specific method is as follows.

NOD-SCID mice without NK cells were used as models and were subcutaneously injected with 0.1 mL LoVo cell suspension (3 million cells). Treatment began after the tumor volume reached 15 $mm^3$. A PBS was used a blank control group and NK92MI cells were used as a negative control group. Each of the mice was injected with 3 million pieces of treating cells via the caudal vein. NK cells which were not modified with the Nb and NK cells which were modified with the Nb were respectively injected via the caudal vein by a number equal to or more than the number of tumor cells during tumor transplantation for a total of 5 times. The injection was given once every two days.

Figure 9:
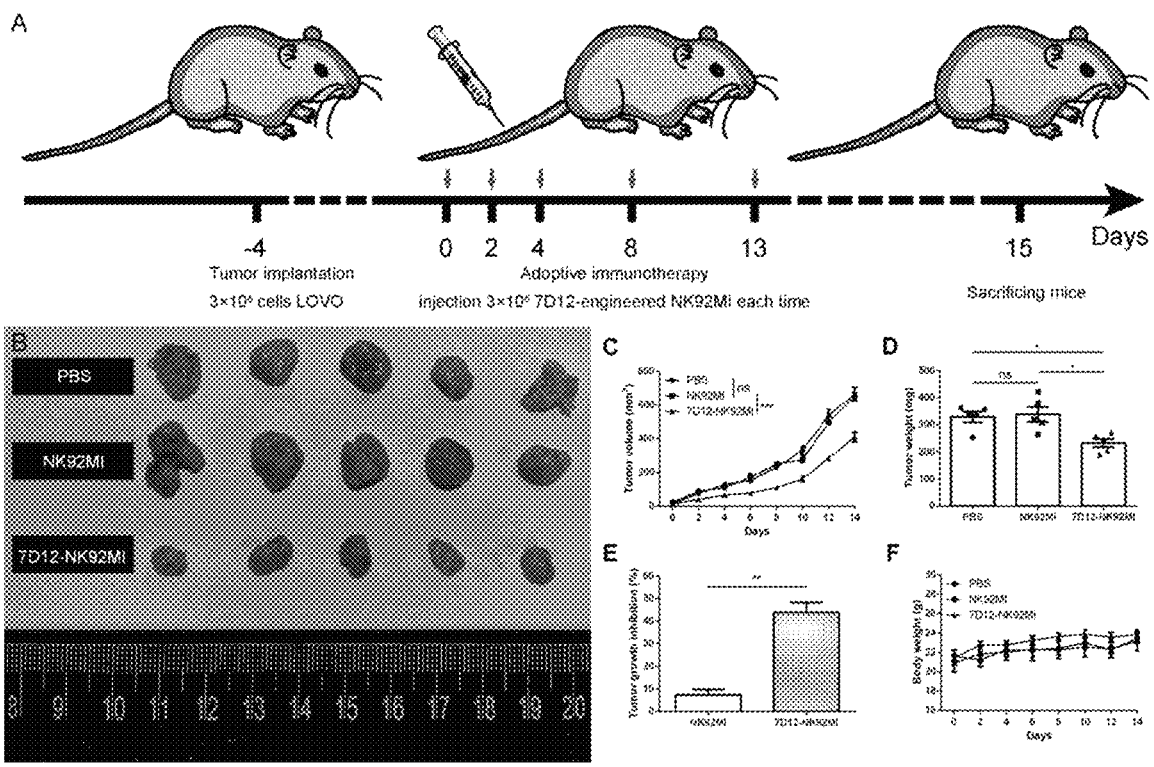
FIG. 9 is a schematic diagram of in-vivo anti-tumor activities of NK92-MI cells modified with the Nb; A is a flowchart of an animal experiment, B is a schematic diagram of real tumors before and after treatment, C is a schematic diagram of changes in the tumor volume during treatment, D is a schematic diagram of comparison of tumor weights before and after the treatment, E is a schematic diagram of a tumor inhibition rate before and after the treatment, and F is a schematic diagram of changes in mouse weight during treatment.

The tumor volume and mouse weight were determined regularly (as shown in FIGS. 9C, F). After two consecutive weeks of treatment, the average tumor volumes of the experimental group, the control group and the PBS group were 410.5 mm$^3$, 647.5 mm$^3$ and 665.7 mm$^3$, respectively. In the entire treatment process, the weight of each of the mice was not obviously changed. Then, the mice ended with euthanasia. Tumors were taken from the mice and weighed (as shown in FIGS. 9B, D). Calculation results showed that the average tumor weights of the experimental group, the control group and the PBS group were 232.8 mg, 338.7 mg and 329.1 mg, respectively. In addition, results showed that, the tumor growth inhibition rate of the NK92MI cells which were not modified with the Nb 7D12 was 7.4%, while the tumor growth inhibition rate of the NK92MI cells which were modified with the Nb 7D12 reached 44%, indicating that the treatment effects of the NK92MI cells engineered with the Nb 7D12 were better (FIG. 9E). Therefore, the treatment group of NK cells which were modified with the Nb had a higher tumor inhibition rate and did not impose great influences on the weight of the mice, indicating that NK cells modified with the Nb achieved a better treatment effect and had higher biological safety at the same time.

The invention discloses an LTCC-based anti-tumor immune cell, a preparation method and use thereof, and belongs to the field of biomedical engineering. Non-natural sugars modified a bioorthogonal reactive group (for example, an azide group, a ketone group) are added into a culture medium of immune cells such as NK cells to obtain immune cells modified with the bioorthogonal reactive group; and then, under a physiological condition, a surface of each of the immune cells is modified with the targeting ligand, for example, a Nb, through the bioorthogonal reaction, wherein the targeting ligand has one terminal with a bioorthogonal reactive pairing group (dibenzocyclooctyne (DBCO), hydroxylamine), which is capable of matching and connecting with the bioorthogonal reactive group, the targeting ligand and the bioorthogonal reactive pairing group are connected by a transpeptidase SrtA-mediated chemoenzymatic method disclosed in the invention, and the targeting ligand has features of high specific recognition and connection with a highly expressed receptor on the surface of each of tumor cells. The immune cell modified with the targeting ligand disclosed in the invention can be specifically connected in a targeted way with the tumor cells, and then the modified immune cell generates and secretes a great number of cytokines which perforate the surfaces of the tumor cells or engulf and lyse tumor cells, so the immune cell modified with the targeting ligand achieves an effect of specifically killing and damaging tumor cells.

The above embodiments are merely preferred embodiments of the invention. It should be noted that, various improvements and modifications made by those ordinarily skilled within the concept of the invention should all fall within the protective scope of the invention.

What is claimed is:

1. A ligand-targeted cell conjugate (LTCC)-based anti-tumor immune cell, characterized in that an immune cell modified with a bioorthogonal reactive group on a surface and a targeting ligand modified with a bioorthogonal reactive pairing group on the surface are correspondingly connected through a bioorthogonal reaction, to form a targeting immune cell, which is conjugated with the targeting ligand on the surface, wherein the targeting ligand performs specific recognition and is connected with a highly expressed receptor on the surface of the tumor cell;

wherein the targeting ligand is Nanobody 7D12 (Nb 7D12);

the targeting immune cell is Natural Killer cell (NK cell);

the bioorthogonal reactive group is an azide group; and the bioorthogonal reactive pairing group is dibenzocyclooctyne (DBCO).

2. The LTCC-based anti-tumor immune cell according to claim 1, wherein the NK cells comprise an NK92-MI cell line, an NK 92 cell line or primary NK cells isolated from human bodies.

3. The LTCC-based anti-tumor immune cell according to claim 1, wherein the bioorthogonal reactive pairing group and the bioorthogonal reactive group on the non-natural sugars are used in pairs.

4. The LTCC-based anti-tumor immune cell according to claim 3, wherein the non-natural sugar is N-azidoacetylmannosamine-tetraacylated (Ac$_4$ManNAz).

\* \* \* \* \*